(12) United States Patent
Brignac

(10) Patent No.: US 7,984,650 B2
(45) Date of Patent: Jul. 26, 2011

(54) PORTABLE ULTRASONIC SCANNER DEVICE FOR NONDESTRUCTIVE TESTING

(75) Inventor: Jacques L. Brignac, Simsbury, CT (US)

(73) Assignee: Alstom Technology Ltd (CH)

( * ) Notice: Subject to any disclaimer, the term of this patent is extended or adjusted under 35 U.S.C. 154(b) by 363 days.

(21) Appl. No.: 12/144,806

(22) Filed: Jun. 24, 2008

(65) Prior Publication Data

US 2009/0316531 A1 Dec. 24, 2009

(51) Int. Cl.
*G01N 29/04* (2006.01)
(52) U.S. Cl. ............... 73/618; 73/620; 73/635; 73/641; 73/866.5
(58) Field of Classification Search .................. 73/618, 73/620, 633, 635, 640, 641, 644, 866.5
See application file for complete search history.

(56) References Cited

U.S. PATENT DOCUMENTS

| | | | |
|---|---|---|---|
| 2,742,259 A | | 4/1956 | Boucher |
| 4,006,359 A | | 2/1977 | Sullins et al. |
| 4,773,426 A | * | 9/1988 | Molnar et al. ............... 600/446 |
| 5,343,750 A | * | 9/1994 | Bashyam ..................... 73/635 |
| 5,359,898 A | | 11/1994 | Latimer |
| 5,454,267 A | | 10/1995 | Moreau |
| 5,476,010 A | | 12/1995 | Fleming et al. |
| 5,549,004 A | | 8/1996 | Nugent |
| 5,619,423 A | | 4/1997 | Scrantz |
| 5,623,107 A | * | 4/1997 | Patterson et al. ............ 73/865.8 |
| 5,805,541 A | * | 9/1998 | Takeda et al. ................ 369/126 |
| 6,271,670 B1 | | 8/2001 | Caffey |
| 6,282,964 B1 | | 9/2001 | Hancock |
| 6,373,914 B1 | | 4/2002 | Gill |
| 6,502,452 B1 | | 1/2003 | Gill |
| 6,567,795 B2 | | 5/2003 | Alouani |
| 6,748,808 B2 | | 6/2004 | Lam et al. |
| 6,799,466 B2 | | 10/2004 | Chinn |
| 6,920,792 B2 | | 7/2005 | Flora |

(Continued)

FOREIGN PATENT DOCUMENTS

DE 19529782 2/1997

(Continued)

OTHER PUBLICATIONS

Harfang Microtechniques Inc. [online]; [retrieved on Sep. 2006]; retrieved from the internet http://www.harfangmicro.com, Boiler Tube Imaging, 2p, Quebec, Que-Canada.

(Continued)

*Primary Examiner* — Jacques M Saint Surin
(74) *Attorney, Agent, or Firm* — Cantor Colburn LLP

(57) ABSTRACT

A scanner device for performing nondestructive testing of a tube includes an ultrasonic probe, a waveguide (wedge) secured relative to the probe, and an encoder secured relative to the probe. The waveguide has a surface contoured in relation to a radius of a tube to be inspected, and the encoder provides a signal indicative of a location of the probe relative to the tube as the probe, waveguide, and encoder are moved in a direction of a longitudinal axis of the tube. In one example, the tube is part of a waterwall, and the surface of the waveguide extends substantially from a web on one side of the tube to a web on the opposite side of the tube. The waveguide may be removably secured relative to the probe such that the waveguide can be replaced with a waveguide having a different surface contour in relation to a different radius of a different tube to be inspected.

15 Claims, 3 Drawing Sheets

U.S. PATENT DOCUMENTS

| | | | |
|---|---|---|---|
| 7,240,556 B2* | 7/2007 | Georgeson et al. | 73/641 |
| 7,315,609 B2* | 1/2008 | Safai et al. | 378/57 |
| 7,693,251 B2* | 4/2010 | Kono et al. | 376/252 |
| 2003/0188589 A1 | 10/2003 | Harthorn et al. | |
| 2009/0027736 A1* | 1/2009 | Brignac et al. | 358/474 |
| 2009/0314089 A1* | 12/2009 | Brignac et al. | 73/622 |
| 2009/0316531 A1* | 12/2009 | Brignac | 367/178 |
| 2010/0185402 A1* | 7/2010 | Pielli et al. | 702/39 |

FOREIGN PATENT DOCUMENTS

| | | |
|---|---|---|
| EP | 0378480 | 10/1990 |
| EP | 1 918 701 | 5/2008 |

OTHER PUBLICATIONS

Russell NDE Systems Inc., [online]; [retrieved 2007]; retrieved from the internet http://www.russelltech.com/ut/DarisMain.html, 2007, An Innovation in Tube Inspection DARIS,1p, Edmonton, Alberta, Canada.

Wikipedia. [online]; [retrieved on Apr. 13, 2007]; retrieved from the Internet http://en.wikipedia.org/wiki/Internal_Rotary_Inspection_System, Internal rotary inspection system 1p.

NDT, [online]; [retrieved on Apr. 13, 2007]; retrieved from the Internet http://www.ndt.net/apcndt2001/papers/7/7/htm Charles Panos, Condition Monitoring-Process Plant Tube Inspection and Ongoing Commitment by Plant Owners and Operators,10p, International Tube Testing Pty Ltd, Qld, Australia.

U.S. Appl. No. 11/751,057, filed May 21, 2007, Title: Boiler Tube Inspection Probe with Centering Mechanism and Method of Operating the Same.

U.S. Appl. No. 11/829,208, filed Jul. 27, 2007, Title: Portable Scanner Device for Metallurgical, Nondestructive Testing.

European Search Report dated Mar. 15, 2011 (EP Appln. No. 09159901.9).

* cited by examiner

PORTABLE ULTRASONIC SCANNER DEVICE FOR NONDESTRUCTIVE TESTING

TECHNICAL FIELD

The present disclosure relates generally to a portable ultrasonic scanner device and, more particularly, to a portable ultrasonic scanner device for use in nondestructive testing.

BACKGROUND

Boiler tube failures are a major cause of forced shutdowns in fossil fuel power plants. As a result of various operational conditions such as heat, pressure, and wear over time, boiler tubes eventually begin to fail by developing circumferential and axial cracks, as well as experience wall thinning (through both erosion and corrosion). When a boiler tube begins to leak, for example, steam escaping through the leak is lost to the boiler environment. Unless the leak is discovered and repaired, the leak may continue to grow until the tube eventually ruptures, thereby forcing the utility operating the boiler to shut it down immediately. These failures prove to be quite expensive for utilities and, as such, early boiler tube leak detection methods are highly desirable.

To this end, there are several technologies available for nondestructive inspection of structure surfaces. For example, in ultrasonic testing, a transducer sends pulse waves into the surface of an object, and receives a return echo indicative of an imperfection. A coupling medium (e.g., liquid) is typically used to provide an effective transfer of ultrasonic wave energy between the transducer and the surface being inspected. In order to conduct an inspection at multiple angles with a single transducer, multiple passes are typically required. Alternatively, phased array ultrasonic sensors utilize a linear or two-dimensional array of ultrasonic transducers that are sequentially pulsed in sequence. Through superposition of individual wavelets, phased arrays provide the capability of steering the angle of the beam. Thus, the beam angle may be set by adjusting the timing of the individual pulses.

Notwithstanding the advantages offered by phased array ultrasonic sensors, tubes used in industrial boilers present a difficult challenge with respect to inspection, as the space surrounding the tubes (and thus access thereto) is typically very limited. In boiler systems, tubes may be interconnected by welding material such that a scanner is unable to complete a circumferential scan of the tubes. In addition, tubes with varying sized geometries render it difficult to provide a one-size-fits-all scanner device.

Accordingly, it would be desirable to provide an improved scanner device for applications such as boiler tube inspection.

SUMMARY

According to the aspects illustrated herein, there is provided a scanner device for performing nondestructive testing of a tube. The scanner device includes an ultrasonic probe, a waveguide secured relative to the probe, and an encoder secured relative to the probe. The waveguide has a surface contoured in relation to a radius of a tube to be inspected, and the encoder provides a signal indicative of a location of the probe relative to the tube as the probe, waveguide, and encoder are moved in a direction of a longitudinal axis of the tube. In one example, the tube is part of a waterwall, and the surface of the waveguide extends substantially from a web on one side of the tube to a web on the opposite side of the tube. The waveguide may be removably secured relative to the probe such that the waveguide can be replaced with a waveguide having a different surface contour in relation to a different radius of a different tube to be inspected. The above described and other features are exemplified by the following figures and detailed description.

BRIEF DESCRIPTION OF THE DRAWINGS

Referring now to the figures, which are exemplary embodiments, and wherein the like elements are numbered alike.

DETAILED DESCRIPTION

A portable scanner device for nondestructive testing of tubes is provided in accordance with exemplary embodiments. The scanner device is compact and adaptable for use with tubes having different diameters, and is particularly useful for scanning waterwall tubes in steam generators (boilers). The scanner device is configured to enable quick change out of probes and ultrasonic (UT) wedges (waveguides), such that multiple inspections of tubes having different diameters are facilitated. The configuration of the scanner device also allows for smooth operation, thereby eliminating or minimizing chatter or skew, as will be described further herein. As used herein, the term "tube" can include any cylindrical body.

Figure 1:
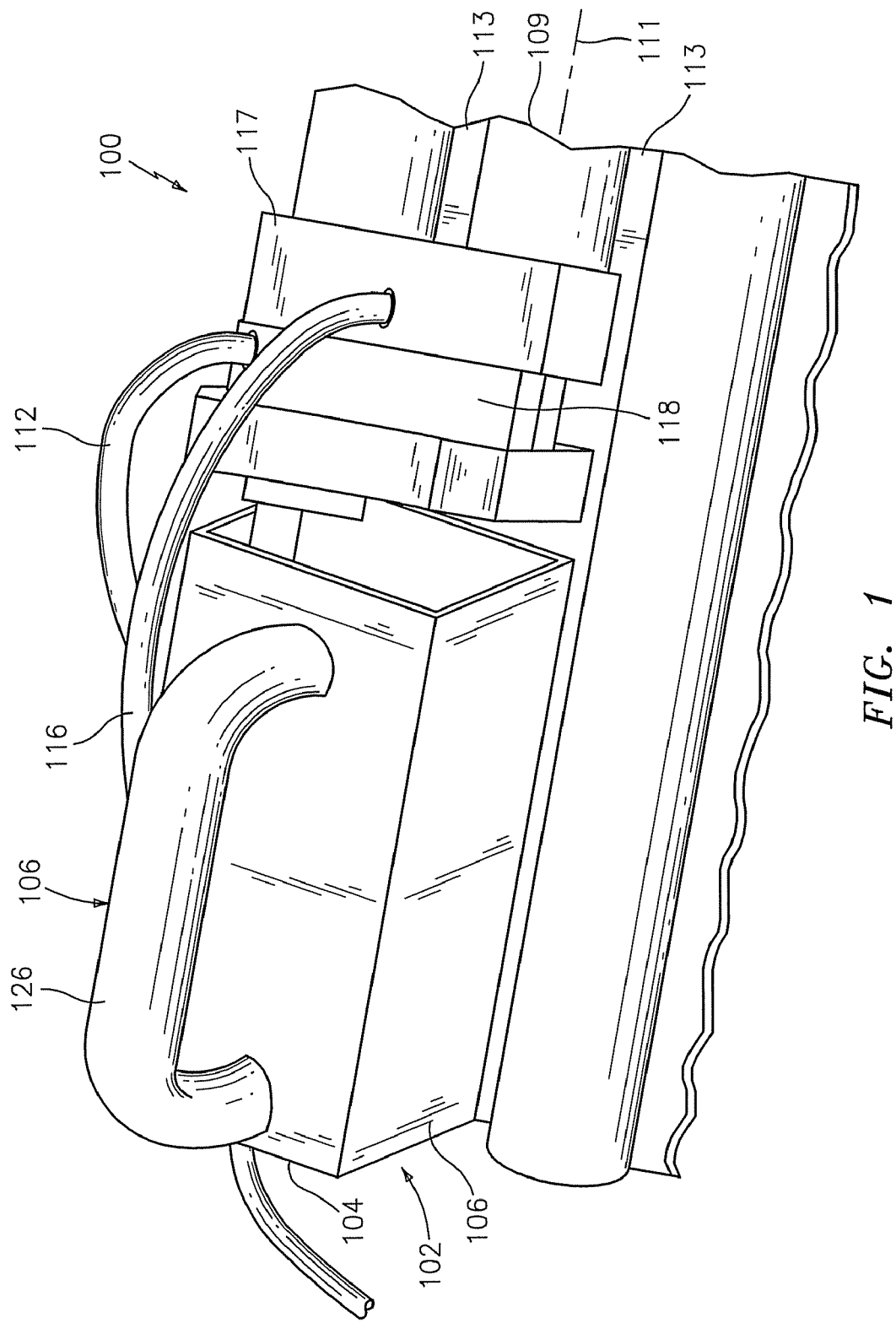
FIG. 1 is a perspective top-side view of a scanner device according to an exemplary embodiment.
Figure 2:
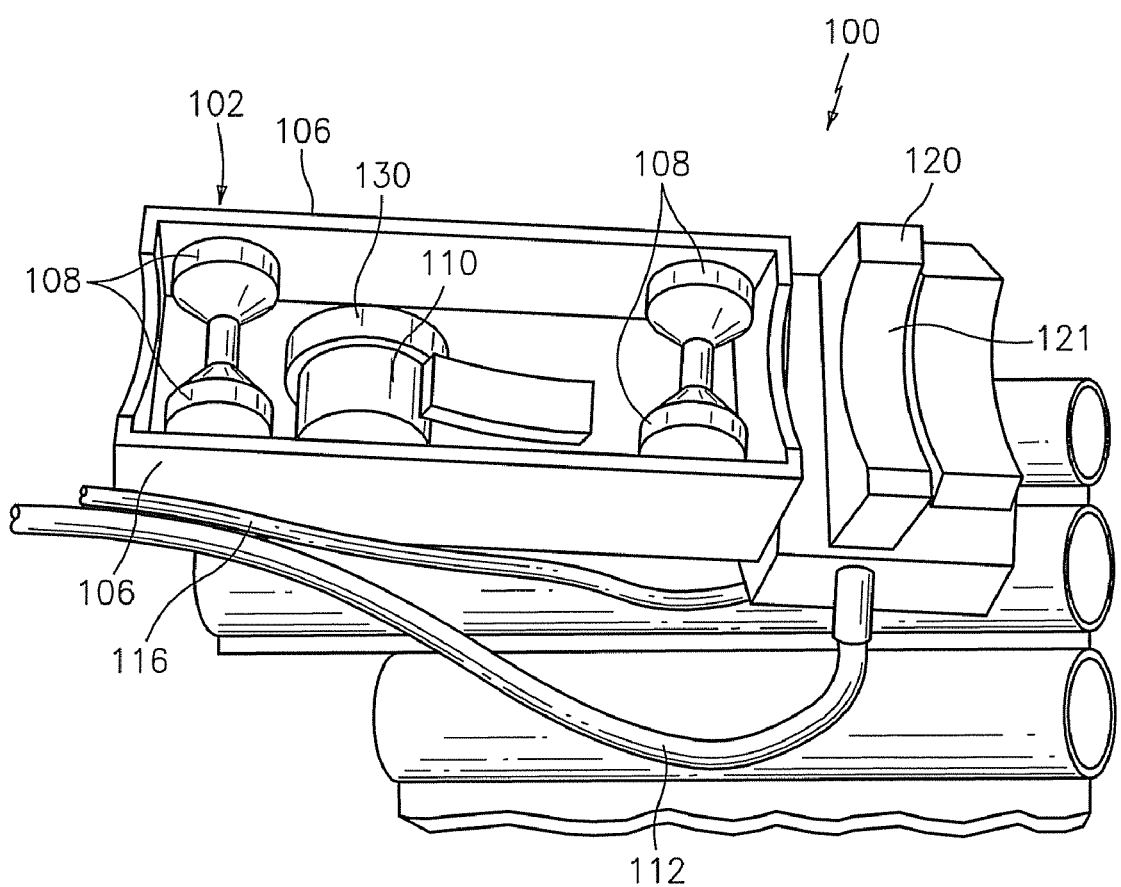
FIG. 2 is a perspective under-side view of the scanner device shown in FIG. 1 in an exemplary embodiment.
Figure 3:
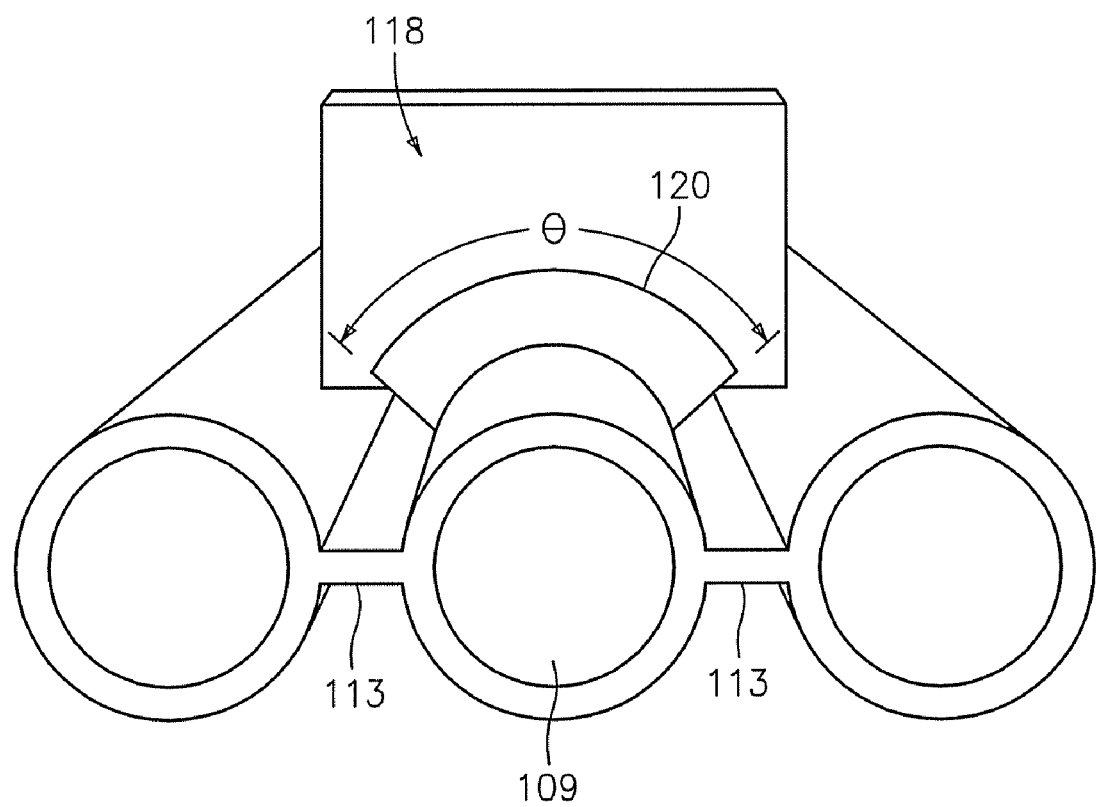
FIG. 3 is a perspective view of a probe and wedge used in the scanner device of FIGS. 1 and 2, in accordance with an exemplary embodiment.

Turning now to FIGS. 1-3, a portable scanner device 100 for performing metallurgical, nondestructive testing of tubes will now be described in accordance with exemplary embodiments. The portable scanner device 100 includes a housing 102 having a top surface 104 and opposing sidewalls 106 extending downward from two edges of the top surface. The top surface 104 and sidewalls 106 may be formed in a substantially planar shape. The scanner device 100 may include at least one handle 126 formed on the upper side of the housing 102 (e.g., on the top surface 104) or one or more of the sidewalls 106. The handle 126 enables testing personnel to manually guide the scanner device 100 on the tube to be tested, as indicated at 109.

Attached to the housing 102 and extending from a first end thereof are an ultrasonic probe 118 and wedge (waveguide) 120. The probe 118 may be an ultrasonic phased array sensor for providing high resolution ultrasonic testing that enables qualitative and quantitative characterizations of identified conditions with respect to tube 109. The probe 118 operates in a known manner by transmitting ultrasonic sound energy (via wedge 120) into a region of the material to be tested, receiving a portion of the energy reflected back by discontinuities in the wave path (such as an crack or imperfection), and transforming the reflected energy into an electrical signal.

The wedge 120 is positioned at an end of the housing 102 and is directly below and in contact with, the probe 118. During operation of the scanner device 100, the wedge 120 contacts the tube 109 via a couplant, as described hereinafter. Wedge 120 may be arranged to scan: in a direction generally perpendicular to a longitudinal axis 111 of tube 109, in a direction generally parallel to longitudinal axis 111, or in both perpendicular and parallel directions.

Advantageously, a surface 121 of the wedge 120 is contoured to the radius of the tube 109, thus allowing a portion of the tube 109 circumference to be scanned. For example, if the tube 109 has a 2.5-inch diameter, the wedge 120 selected for use with the scanner device 100 will have about a 2.5-inch contoured radius. This is particularly advantageous where tube 109 is part of a waterwall, as depicted in the Figures. In a waterwall, tubes 109 are coupled in side-by-side fashion by steel webs (membranes) 113. The contour of the wedge 120 allows the probe 118 to scan substantially the entire portion of the tube 109 from the web 113 on one side of the tube 109 to web 113 on the other side of the tube 109. When viewed in the direction of longitudinal axis 111, the wedge 120 covers θ degrees of the tube 109. In the example shown, the angle θ is about 120 degrees. It is contemplated that the angle θ may be between about 90 and 170 degrees, although the angle used depends on the surface to be tested and the type of probe used. Because the wedge 120 covers substantially the entire portion of the tube 109 from the web 113 on one side of the tube 109 to web 113 on the other side of the tube 109, scanner device 100 can scan a waterwall tube without the need for side-to-side motion and the potential for test errors inherent in such motion. The wedge is detachable, and may be interchanged with wedges having different scan directions and contour radii. The detachability of the probe 118 provides for quick change out of the various wedge 120 sizes that may be required for the varying sizes of tubes under inspection.

The probe 118 includes a cable 112 extending therefrom. The cable 112 is operable for transmitting electrical signals between the probe 118 and a computer device (e.g., a general purpose computer) having memory to record the electrical signals received from the probe 118 and display screen to allow an operator to view a visual indication of the electrical signals received from the probe 118. Using various applications, the data acquired and recorded from the inspection may be converted in graphical form and displayed by computer device. The graphical form of the data may illustrate qualitative and quantitative results of the inspections via the ultrasonic probe 118. For example, the results may include defects in the weld under inspection, as well as the extent of the defects (such as size, range, and depth).

The scanner device 100 also includes a couplant tube 116 having a first end connected to a couplant supply source (e.g., pressurized container or pump) and a second end connected to a couplant manifold 117 disposed at the first end of the housing 102. The couplant tube 116 receives couplant from the supply source (not shown) and delivers the couplant to the couplant manifold 117, which in turn, delivers the couplant directly on the tube 109 at the inspection location. The couplant material may be water, gel, or other suitable material to facilitate the transmission of ultrasonic waves between the probe 118 and tube 109.

An encoder 110 is attached to the bottom of the housing 102. The encoder 110 is operable for providing a reference point for a physical location at which the inspection is initiated, as well as a means for tracking and recording the responses from the probe 118 with respect to the ongoing inspection. In the example shown, the encoder 110 includes a wheel 130 that rests on the tube 109 and rotates as the scanner device 100 is moved relative to the tube 109. A sensor within the encoder 110 detects movement of the wheel, which indicates the relative position of the probe 118 as it moves along the tube 109. The encoder 110 provides electrical signals indicative of this position to the computer device via cable 112, thus allowing the computer device to correlate probe 118 readings with specific locations on tube 109.

Also attached to the housing 102 are wheels 108, which are disposed on the bottom of the housing 102. The wheels 108 have an axis of rotation that extends generally perpendicular to the longitudinal axis of the tube 111 to allow the scanner device 100 to move in the direction of the longitudinal axis 111. The wheels 108 may be magnetic for securing the scanner device 100 to the tube 109 during testing. In one embodiment, two sets of two wheels 108 are each integrally formed and have a tapered midsection, such that they are widest at the wheel portions and thinnest at the midsection. The wheels 108 may be detachably fixed to the housing 102, and the scanner device 100 may be configured to receive different sets of wheels 108 having different angles of taper, each of which corresponds to a width and arc of the tube 109 under inspection. During operation, two sets of wheels 108 having the same angle of taper are disposed in the housing 102 in accordance with the width and arc of the tube 109. When the operator finishes with the current test subject and moves on to a different tube 109 having a different width and arc (e.g., smaller or larger diameter tubing), the operator need only disconnect the wheels 108 and replace them an appropriate set of wheels 108 having the corresponding angle of taper.

While the scanner device 100 is depicted as including a handle 126 to move the scanner device 100 along the tube 109, it is contemplated that the scanner device 100 may include a motor (not shown) for driving the wheels 108, and a power source, such as a battery (not shown), that provides power to the motor. However, the portability of the scanner device 100 may be increased without the added weight of the motor.

As described above, the scanner device is compact and adaptable for use with tubes, particularly waterwall tubes, of different diameters. The scanner device is configured to enable quick change out of probes and ultrasonic (UT) wedges, such that multiple inspections of test subjects having varying sizes are easily and quickly facilitated. The configuration of the scanner device also allows for smooth operation, thereby eliminating or minimizing chatter or skew.

While the invention has been described with reference to various exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A scanner device for performing nondestructive testing of a tube, comprising:
   an ultrasonic probe;
   a waveguide secured relative to the probe, the waveguide having a surface contoured in relation to a radius of a tube to be inspected;
   an encoder secured relative to the probe, wherein the encoder provides a signal indicative of a location of the probe relative to the tube as the probe, waveguide, and encoder are moved in a direction of a longitudinal axis of the tube; and
   wheels secured to the probe, waveguide, and encoder, the wheels operable for facilitating movement in the direction of the longitudinal axis, and the wheels having an angled taper that corresponds to the circumference of the tube.

2. The scanner device of claim 1, wherein the wheels are removable from the probe, waveguide, and encoder to facilitate tubes having different diameters.

3. The scanner device of claim 1, wherein the wheels are magnetic.

4. The scanner device of claim 1, wherein the probe, waveguide, and encoder are secured to a handle for manually moving the scanner device in the direction of the longitudinal axis.

5. The scanner device of claim 1, further comprising a couplant tube secured relative to the waveguide, the couplant tube being arranged to direct a couplant material proximate the waveguide as the waveguide moves in the direction of the longitudinal axis.

6. The scanner device of claim 1, wherein the ultrasonic probe is a phased array probe.

7. The scanner device of claim 1, wherein the probe, waveguide, and encoder are secured to a motor for moving the scanner device in the direction of the longitudinal axis.

8. The scanner device of claim 1, wherein the probe, waveguide, and encoder are secured to a common housing.

9. The scanner device of claim 1, wherein the wave guide directs ultrasonic signals from the probe in at least one of: a direction generally perpendicular to the longitudinal axis of the tube and a direction generally parallel to the longitudinal axis of the tube.

10. The scanner device of claim 1, wherein the tube is part of a waterwall, and the surface of the waveguide extends substantially from a web on one side of the tube to a web on the opposite side of the tube.

11. The scanner device of claim 10, wherein the surface of the waveguide covers between about 90 to about 170 degrees of the tube when viewed in the direction of the longitudinal axis.

12. The scanner device of claim 11, wherein the surface of the waveguide covers about 120 degrees of the tube when viewed in the direction of the longitudinal axis.

13. The scanner device of claim 1, wherein the surface of the waveguide covers between about 90 to about 170 degrees of the tube when viewed in the direction of the longitudinal axis.

14. The scanner device of claim 13, wherein the surface of the waveguide covers about 120 degrees of the tube when viewed in the direction of the longitudinal axis.

15. The scanner device of claim 1, wherein the waveguide is removably secured relative to the probe such that the waveguide may be replaced with a waveguide having a different surface contour in relation to a different radius of a different tube to be inspected.

\* \* \* \* \*

UNITED STATES PATENT AND TRADEMARK OFFICE
CERTIFICATE OF CORRECTION

| | | |
|---|---|---|
| PATENT NO. | : 7,984,650 B2 | Page 1 of 1 |
| APPLICATION NO. | : 12/144806 | |
| DATED | : July 26, 2011 | |
| INVENTOR(S) | : Jacques L. Brignac | |

It is certified that error appears in the above-identified patent and that said Letters Patent is hereby corrected as shown below:

In column 5, line 19, in claim 9, delete "wave guide" and insert -- waveguide --, therefor.

Signed and Sealed this
First Day of January, 2013

David J. Kappos
*Director of the United States Patent and Trademark Office*